United States Patent [19]
Kobayashi et al.

[11] Patent Number: 5,512,758
[45] Date of Patent: Apr. 30, 1996

[54] FLUORESCENCE DETECTION APPARATUS

[75] Inventors: Takao Kobayashi; Katsutoshi Sakai; Kenzou Kobayashi, all of Tokyo, Japan

[73] Assignee: Furukawa Electric Co., Ltd., Tokyo, Japan

[21] Appl. No.: 234,291

[22] Filed: Apr. 28, 1994

[30] Foreign Application Priority Data

| Apr. 27, 1993 | [JP] | Japan | 5-123526 |
| May 21, 1993 | [JP] | Japan | 5-142924 |
| May 31, 1993 | [JP] | Japan | 5-152705 |

[51] Int. Cl.$^6$ .................................................. G01N 21/64
[52] U.S. Cl. .............................. 250/461.1; 250/458.1
[58] Field of Search ............................... 250/372, 458.1, 250/461.1, 459.1

[56] References Cited

U.S. PATENT DOCUMENTS

| 3,963,351 | 6/1976 | Chance et al. | 250/458.1 X |
| 4,448,547 | 5/1984 | Wickersheim | 250/461.1 X |
| 4,617,467 | 10/1986 | Senftle et al. | 250/461.1 |
| 4,708,494 | 11/1987 | Kleinerman | 250/458.1 X |
| 4,816,686 | 3/1989 | Hara et al. | 250/459.1 X |
| 5,108,932 | 4/1992 | Wolfbeis | 250/458.1 X |

FOREIGN PATENT DOCUMENTS

| 440342 | 8/1991 | European Pat. Off. | 250/458.1 |

Primary Examiner—Carolyn E. Fields
Assistant Examiner—Edward J. Glick
Attorney, Agent, or Firm—Knobbe, Martens, Olson & Bear

[57] ABSTRACT

A fluorescence detection apparatus for differentiating an object containing a fluorescent substance by detecting fluorescence emitted by the fluorescent substance, which apparatus includes: an excitation light source which emits ultraviolet light that excites a fluorescent substance; a light detector for detecting fluorescence; and an optical guiding system consisting essentially of a single glass block of an angular columnar shape having: an incidence face located on a side of the glass block, through which the ultraviolet light enters; a reflection and emission face constituted by an inclined face, from which the incident ultraviolet light reflects toward the object, and through which florescence emitted from the object passes toward the light detector; and a detection face at the bottom of the glass block facing the object, through which the ultraviolet light exits and hits the object, and through which florescence emitted from the object enters, thereby allowing for reduction in the size of the apparatus, easy positioning of the glass block, and minimizing the effects of object vibration.

17 Claims, 6 Drawing Sheets

$\theta_g = 90° + \theta$

REFLECTION  λt  PASSAGE

FLUORESCENCE DETECTION APPARATUS

BACKGROUND OF THE INVENTION

1. Field of the Invention

The present invention relates to a fluorescence detection apparatus used for detecting fluorescence emitted from a fluorescent substance in or on paper, such as paper money printed with or including a fluorescent substance for the purpose of discrimination or including a fluorescent substance for purposes of judging the genuineness of the paper.

2. Description of the Related Art

Paper money, securities, and other important documents (paper) are often forged. It has become important to take steps to prevent forgery and to judge the non-genuineness of forgeries.

For example, some of the paper money and other paper documents issued and in circulation in the world are printed with a or include fluorescent substance for the purposes of forgery detection. More specifically, there is paper which is printed in a design or pattern with an ink including a fluorescent substance as well as paper including a thread like fluorescent substance (fluorescent thread) within it and printed with ordinary ink.

To judge the genuineness of such paper, there has been known in the past the method of irradiating paper containing a fluorescent substance (hereinafter referred to as the "examined object") with ultraviolet light as excitation light, detecting the fluorescence emitted from the fluorescent substance of the examined object due to the irradiation, and judging the pattern (discriminating) of the detected signals.

Further, along with the improvement in the performance of copying machines, paper money is now sometimes forged using copying technology. As the method for judging the non-genuineness of such forged paper money, there is known the method of judging paper money to have been forged by copying if fluorescence is detected from the examined object, since the white paper commercially sold for copier use (copy paper) includes a fluorescent whitener, and the paper used for paper money generally does not include a fluorescent substance.

As a basic method for detecting such a fluorescent substance, for example, there is proposed the method shown in FIG. 1 and FIG. 2, as disclosed in Japanese Patent Application No. 5-123526.

In FIG. 1 and FIG. 2, a black light, ultraviolet (UV) lamp, or other excitation light source 101 has disposed in front of it an optical filter 102 which passes the range of wavelength range of the excitation light, but blocks the unnecessary range, in particular the visible light range. Excitation light is irradiated through the optical filter 102 and a detection window 106 to the paper or other examined object 103. The excitation light from the excitation light source 101 which passes through the optical filter 102 causes the emission of visible light from the fluorescent substance of the ink printed on the surface of the examined object 103 or the fluorescent thread etc. woven into the examined object 103. This visible light and the excitation light reflected at the surface of the examined object 103 (surface reflected light) passes through the optical filter 104, which blocks the region of the wavelength shorter than ultraviolet light, and the desired reflected light is detected by a light receiving unit 105.

The signals detected by the light receiving unit 105 are subjected to pattern matching at a judgement apparatus (not shown). That is, the judgement apparatus compares the pattern detected by the light receiving unit 105 and a reference pattern stored in the judgement apparatus and judges the genuineness of the examined object 103 from the coincidence or non-coincidence of the patterns.

The magnitude of the fluorescence emitted by the fluorescent substance of the examined object 103 is extremely low compared with the excitation light from the excitation light source 101, sunlight entering the system from around the examined object 103, stray light from light bulbs, etc.

Therefore, in the past, use was made of a plurality of optical filters for the optical filter 102 and the optical filter 104 so as to block the excitation light, sunlight, stray light, etc., block even the reflection of excitation light at the surface of the examined object 103 and the glass detection window 106 etc., and pass only the desired wavelength of light.

However, if use is made of a plurality of optical filters, a holder for precisely holding the components in the fluorescence detection apparatus at their proper positions of disposition becomes necessary, resulting in problems with complexity of construction of the fluorescence detection apparatus. Further, the thickness of the glass itself making up the optical filters, limits how small the fluorescence detection apparatus can be made and there consequently was a tendency for the fluorescence detection apparatus to be large.

Further, the examined object 103 is transported to the detection window 106 where it is irradiated by ultraviolet light, but since it moves during transport (vibrates), the length of the optical path between the detection window 106 and the examined object 103 changes. Further, the angle of incidence and angle of reflection of the ultraviolet light on and from the examined object 103 fluctuate as well, so the optical axis changes. Accordingly, a high degree of precision is required for the positioning of the optical system inside the fluorescence detection apparatus. The positioning work requires a degree of skill, and the work was troublesome.

Further, when the surface of the examined object 103 is not printed with a fluorescent substance, but the fluorescent substance is included inside the object, no fluorescence will be emitted even if ultraviolet light is irradiated on the surface of the examined object 103 and thus there was the problem that the genuineness of the examined object 103 could not be judged.

SUMMARY OF THE INVENTION

An object of the present invention is to provide a compact fluorescence detection apparatus.

Another object of the present invention is to provide a fluorescence detection apparatus which prevents vibration during transport of the paper on which the fluorescent substance is printed or including the fluorescent substance (examined object) to keep the length of the optical path from changing and thereby improve the precision of detection of the fluorescence.

Another object of the present invention is to provide a fluorescence detection apparatus which does not require positioning of the optical system, by use of simple construction.

A further object of the present invention is to provide a fluorescence detection apparatus which detects both the reflected fluorescence and transmitted fluorescence emitted from the fluorescent substance of the examined object so as to enable more accurate detection of fluorescence.

A still further object of the present invention is to provide a fluorescence detection apparatus which enables a more accurate judgement of the genuineness of the examined object.

According to a first aspect of the present invention, there is provided a fluorescence detection apparatus which irradiates ultraviolet light to an examined object including a fluorescent substance to cause it to emit fluorescence and which detects that fluorescence, including:

a single glass block of an angular columnar shape which does not fluoresce under ultraviolet light and has one inclined face having a reflection and emission face constituted by the inclined face, a flat detection face which substantially faces the reflection and emission face and perpendicularly intersects with the longitudinal direction of the angular columnar shape, and an incidence face which continues from the reflection and emission face to the detection face, an excitation light source which emits light including ultraviolet light and which is provided near the incidence face of the glass block so that the light from the excitation light source is made incident on the glass block from the incidence face, and a light detector which is provided near the reflection and emission face of the glass block so as to receive fluorescence emitted from the reflection and emission face, the detection face of the glass block being made to face a flat examined object including a fluorescent substance, the reflection and emission face of the glass block being treated to reflect ultraviolet light and pass fluorescence, and the detection face of the glass block being treated to pass ultraviolet light and pass fluorescence.

More specifically, (a) the incidence face of the glass block may be treated to pass only ultraviolet light or (b) an optical filter passing only ultraviolet light may be provided between the incidence face of the glass block not functioning to block visible light and the excitation light source.

According to a second aspect of the present invention, there is provided a fluorescence detection apparatus which irradiates ultraviolet light to an examined object including a fluorescent substance to cause it to emit fluorescence and which detects that fluorescence, including:

a single glass block of an angular columnar shape which does not fluoresce under ultraviolet light and has one inclined face and which has an incidence and reflection face constituted by the inclined face, a flat detection face which substantially faces the incidence and reflection face and perpendicularly intersects with the longitudinal direction of the angular columnar shape, and an emission face which continues from the incidence and reflection face to the detection face, an excitation light source which emits light including ultraviolet light and which is provided near the incidence and reflection face of the glass block so that the light from the excitation light source is made incident on the incidence and reflection face, and a light detector which is provided near the emission face of the glass block so as to receive light from the emission face, the detection face of the glass block being made to face a flat examined object including a fluorescent substance, the incidence and reflection face of the glass block being treated to pass ultraviolet light and reflect fluorescence, the detection face of the glass block being treated to pass ultraviolet light and pass fluorescence, and the mission face of the glass block being treated to reflect ultraviolet light and pass fluorescence.

According to a third aspect of the present invention, there is provided a fluorescence detection apparatus which irradiates ultraviolet light to an examined object including a fluorescent substance to cause it to emit fluorescence and which detects that fluorescence, including:

a single glass block of an angular columnar shape which does not fluoresce under ultraviolet light and has one inclined face and which has a reflection and emission face constituted by the inclined face, a flat detection face which substantially faces the reflection and emission face and perpendicularly intersects with a longitudinal direction of the angular columnar shape, and an incidence face which continues from the reflection and emission face to the detection face, an excitation light source which emits light including ultraviolet light and which is provided near the incidence face of the glass block so that the light from the excitation light source is made incident on the incidence face, a light detector which is provided near the reflection and emission face of the glass block so as to receive fluorescence from the reflection and emission face, and a second excitation light source which is provided at a position facing the detection face of the glass block sandwiching the examined object and which emits light including ultraviolet light, the detection face of the glass block being made to face a flat examined object including a fluorescent substance, the reflection and emission face of the glass block being treated to reflect ultraviolet light and pass fluorescence, and the detection face of the glass block being treated to pass ultraviolet light and pass fluorescence.

Preferably, provision is made, between the second excitation light source and the examined object, of a second optical filter for blocking the visible light component included in the light emitted from the second excitation light source and allowing only ultraviolet light to irradiate the examined object.

More preferably, (a) the incidence face of the glass block may be treated to pass only ultraviolet light or (b) an optical filter passing only ultraviolet light may be provided between the incidence face of the glass block not functioning to block visible light and excitation light source.

According to a fourth aspect of the present invention, there is provided a fluorescence detection apparatus which irradiates ultraviolet light to an examined object including a fluorescent substance to cause it to emit fluorescence and which detects that fluorescence, including:

a single glass block of an angular columnar shape which does not fluoresce under ultraviolet light and has one inclined face and which has an incidence and reflection face constituted by the inclined face, a flat detection face which substantially faces the incidence and reflection face and perpendicularly intersects with a longitudinal direction of the angular columnar shape, and an emission face which continues from the incidence and reflection face to the detection face, an excitation light source which emits light including ultraviolet light and which is provided near the incidence and reflection face of the glass block so that the light from the excitation light source is made incident on the incidence and reflection face, a light detector which is provided near the emission face of the glass block so as to receive fluorescence from the emission face, and a second excitation light source which is provided at a position facing the detection face of the glass block sandwiching the examined object and which emits light including ultraviolet light, the detection face of the glass block being made to face a flat examined object including a fluorescent substance, the incidence and reflection face of the glass block being treated to pass ultraviolet light and reflect fluorescence, the detection face of the glass block being treated to pass ultraviolet light and pass fluorescence, and the emission face of the glass block being treated to reflect ultraviolet light and pass fluorescence.

Preferably, provision is made, between the second excitation light source and the examined object, of a second optical filter for blocking the visible light component included in the light emitted from the second excitation light source and allowing only the ultraviolet light to irradiate the examined object.

According to a fifth aspect of the present invention, there is provided a fluorescence detection apparatus which irradiates ultraviolet light to an examined object including a fluorescent substance to cause it to emit fluorescence and which detects that fluorescence, including:

a bent single glass block which does not fluoresce under ultraviolet light, provided with an inclined face at a center bent portion, having an incidence face formed at one of the end faces of the glass block bent at the bent portion so as to receive the ultraviolet light, having a detection face formed at the other end face of the glass block bent at the bent portion so as to pass ultraviolet light and fluorescence, and having an angle $\theta_g$ of the inclined face defined so as to reflect ultraviolet light and pass fluorescence, an excitation light source which emits light including ultraviolet light and which is provided near the incidence face of the glass block so that the light is made incident on the incidence face, and a light detector which is provided near the inclined face of the glass block so as to receive fluorescence from the inclined face, the detection face of the glass block being made to face a flat examined object including a fluorescent substance.

More specifically, the angle $\theta_g$ of the inclined face of the glass block is defined by the following equation:

$$\theta_g = 90° + \sin^{-1}(n_a/n_t)$$

where $n_a$ is the index of refraction of the medium between the inclined face and the light detector and $n_t$ is the index of refraction of the glass block Preferably, the incidence face of the glass block is treated to block the visible light component included in the light emitted from the excitation light source and to pass only the ultraviolet light component.

More preferably, provision is made, between the excitation light source and the incidence face of the glass block, of an optical filter for blocking the visible light component included in the light emitted from the excitation light source and allowing only the ultraviolet light component to pass.

According to a sixth aspect of the present invention, there is provided a fluorescence detection apparatus which irradiates ultraviolet light to an examined object including a fluorescent substance to cause it to emit fluorescence and which detects that fluorescence, including:

a bent single glass block which does not fluoresce under ultraviolet light, provided with an inclined face at a center bent portion, having an emission face formed at one of the end faces of the glass block bent at the bent portion so as to pass the ultraviolet light, having a detection face formed at the other end face of the glass block bent at the bent portion so as to pass ultraviolet light and fluorescence, and having an angle $\theta_g$ of the inclined face defined so as to reflect ultraviolet light and pass fluorescence, an excitation light source which emits light including ultraviolet light and which is provided at a position facing the detection face of the glass block sandwiching the examined object including the fluorescent substance so as to irradiate ultraviolet light to the examined object, a light detector which is provided near the inclined face of the glass block so as to receive fluorescence from the inclined face, and an excitation light detector provided near the emission face of the glass block so as to receive the ultraviolet light from the emission face, the detection face of the glass block being made to face the examined object.

According to a seventh aspect of the present invention, there is provided a fluorescence detection apparatus which irradiates ultraviolet light to an examined object printed with a fluorescent substance to cause it to emit fluorescence and which detects that fluorescence, including:

a single glass block which does not fluoresce under ultraviolet light and is provided with a first face a second face and a third face, an excitation light source which is provided near the first face of the glass block and makes the light including the ultraviolet light incident on the glass block, and a light detector which is provided near the third face of the glass block and receives the fluorescence emitted from the third face, the examined object being disposed transportably facing the second face of the glass block, and the fluorescent substance of the examined object being excited and made to emit fluorescence by ultraviolet light incident from the excitation light source to the glass block, which fluorescence is guided into the glass block and made incident from the third face to the light detector.

Preferably, provision is made of a second excitation light source provided at a position facing the second face of the glass block sandwiching the examined object and making the light including the ultraviolet light incident on the glass block.

BRIEF DESCRIPTION OF THE DRAWINGS

The above objects and features and other objects and features of the present invention will become clearer from the following description made in reference to the appended drawings, in which.

DESCRIPTION OF THE PREFERRED EMBODIMENTS

The first embodiment of the fluorescence detection apparatus of the present invention will be described first with reference to FIG. 3.

Figure 3:
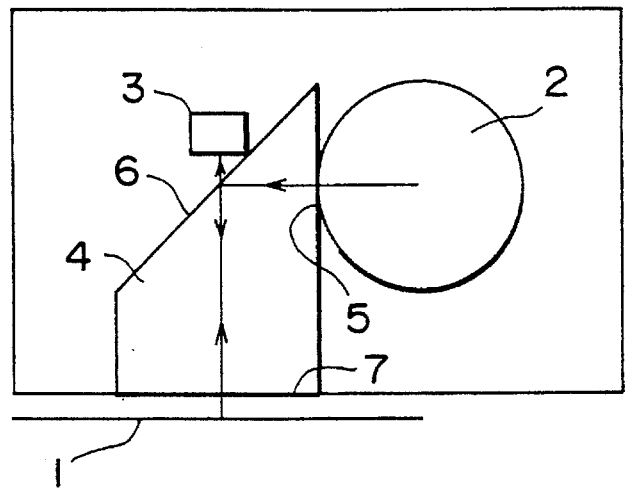
FIG. 3 is a view of the configuration of a first embodiment of the fluorescence detection apparatus of the present invention.

FIG. 3 is a sectional view of the fluorescence detection apparatus of the first embodiment of the present invention. The fluorescence detection apparatus has an excitation light source 2, a light detector 3, and a glass block 4.

The fluorescence detection apparatus judges the genuineness of an examined object 1 by irradiating excitation light on the examined object 1 and detecting the fluorescence emitted by the examined object 1. A judgement apparatus for judging the genuineness of the examined object 1 using this detected fluorescence is connected to the fluorescence detection apparatus, but is not shown.

Figure 1:
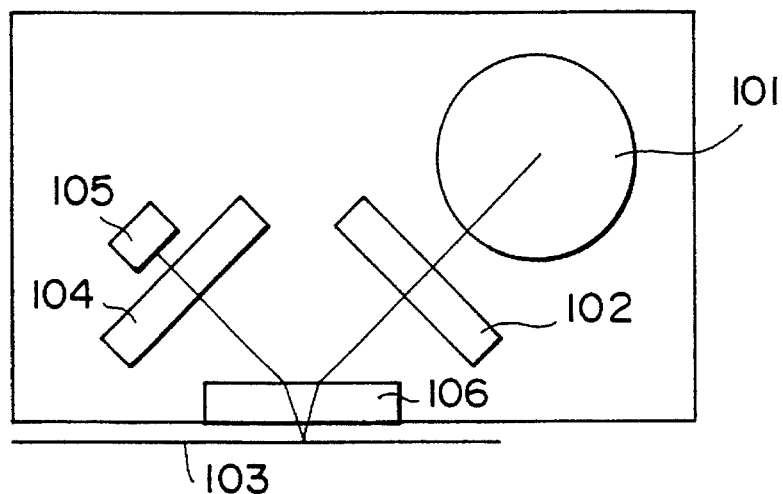
FIG. 1 is a view of an example of the configuration of a fluorescence detection apparatus of a related art.
Figure 2:
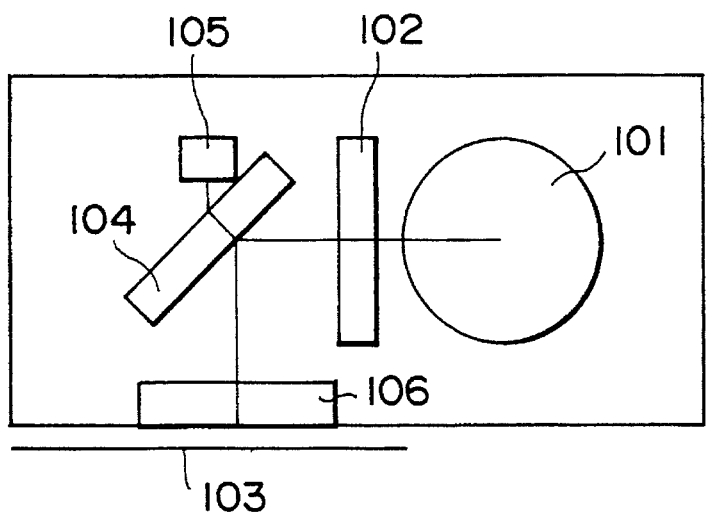
FIG. 2 is a view of an example of the configuration of a fluorescence detection apparatus of an another related art.

Comparing the fluorescence detection apparatus illustrated in FIG. 1 and FIG. 2 and the fluorescence detection apparatus illustrated in FIG. 3, the excitation light source 101 shown in FIG. 1 and FIG. 2 and the excitation light source 2 shown in FIG. 3 are substantially the same and the light receiver 105 and the light detector 3 are substantially the same as well. However, the fluorescence detection apparatus shown in FIG. 3 is not provided with the optical filter 102 and the optical filter 104 showing the plurality of optical filters illustrated in FIG. 1 and FIG. 2 and is not provided with the detection window 106. In the fluorescence detection apparatus shown in FIG. 3, a single glass block 4 is used in place of these members 102, 104, and 106.

The glass block 4 of the fluorescence detection apparatus shown in FIG. 3 is disposed between the excitation light source 2 and the examined object 1 and light detector 3. These elements 2, 1, and 3 are optically coupled. By the use of this single glass block 4, the optical system is made smaller and the construction simpler. Further, the positioning work of the optical system becomes simpler.

Further, to prevent vibration of the examined object 1 in the transport direction of the examined object 1, the flat face of the detection face 7 of the glass block 4 is made to face the examined object 1, and the excited light is emitted perpendicular to the examined object 1.

In this embodiment, further, the excitation light source 2, which has the largest external dimensions among the components of the fluorescence detection apparatus, is disposed in the lateral direction of the glass block 4 so as to reduce the height of the apparatus, making it more compact.

As the examined object 1, for example, there is paper money and other types of papers including a fluorescent substance or printed with a fluorescent substance.

The excitation light source 2 is a light source for emitting excitation light including ultraviolet light for irradiating the examined object i to cause it to emit fluorescence. The excitation light source 2 is disposed at the outer side of the incidence face 5 of the glass block 4. As the excitation light source 2, use is made of an ultraviolet light (UV) lamp etc.

The light detector 3 is disposed at the outer side of the reflection and emission face 6 of the glass block 4 so as to receive the fluorescence from the examined object 1. As this light detector 3, use is made of an opto-electric (O/E) converter able to receive light of fluorescent wavelength for example.

Figure 4:
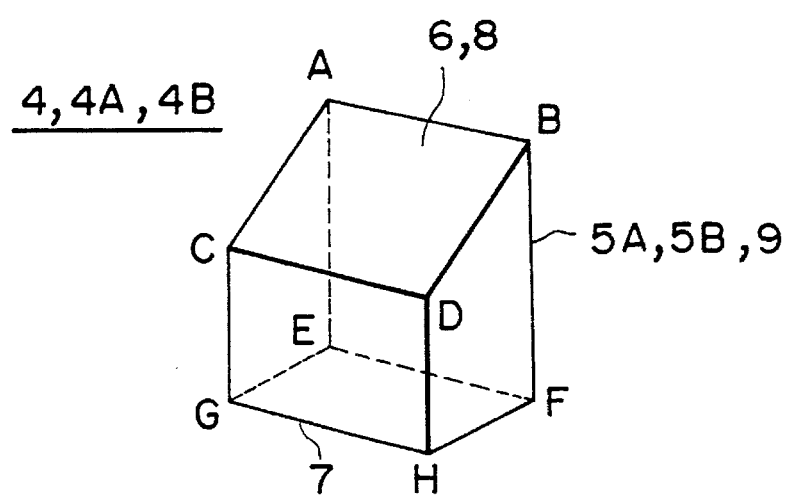
FIG. 4 is a perspective view of the glass block illustrated in FIG. 3, FIGS. 5A and 5B are views of the configuration of a second embodiment of the fluorescence detection apparatus of the present invention.

A perspective view of the glass block 4 is given in FIG. 4.

The glass block 4 is a single glass block of an angular columnar shape with an inclined top face and a flat bottom face and does not fluoresce under ultraviolet light. Synthetic quartz glass for example is a suitable material.

The glass block 4 has an incidence face 5 in proximity with the excitation light source 2, a reflection and emission face 6 which inclines and faces the light detector 3, and a flat detection face 7 which faces the examined object 1.

As illustrated in FIG. 4, the ABEF face of the glass block 4 is defined as the incidence face 5, on which is provided by evaporation etc. a film having a filtering function blocking the visible light component of the excitation light incident on the face and passing only the ultraviolet light component. When the excitation light emitted from the excitation light source 2 does not include a visible light component and includes only ultraviolet light, the incidence face 5 may be a simple glass face with no filtering function.

The inclined face of the glass block 4, that is, the ABDC face, is defined as the reflection and emission face 6, which is provided by evaporation etc. with a film having a filtering function reflecting the ultraviolet light at its inside face, but passing the fluorescence emitted from the fluorescent substance of the examined object 1.

The EFHG face of the glass block 4 is defined as the flat, which detection face 7 is provided parallel to and near the examined object 1. This performs the function of the above-mentioned detection window 106 and performs the function of restricting the transport vibration of the examined object 1. The detection face 1 has an optical characteristic of passing the excitation light (ultraviolet light) reflected by the reflection and emission face 6, irradiating it on the examined object 1, and enabling the passage of the fluorescence emitted from the fluorescent substance of the examined object 1 under the irradiation. Note that the detection face 7 is disposed close to the detected face of the examined object 1 in parallel with the same and that the excitation light emitted from the detection face 7 is irradiated perpendicularly with respect to the detected face of the examined object 1. As a result, it is possible to prevent a change in the length of the optical path with respect to the examined object 1.

Further, if the excitation light (ultraviolet light) from the excitation light source 2 is made incident on the reflection and emission face 6 at an angle of 45 degrees, and the angle formed by the optical axis of the excitation light incident on the examined object 1 becomes 90 degrees, the fluorescence from the examined object 1 becomes superimposed on the same line as the optical axis of the excitation light to the detection face, 1 except reversed in direction 180 degrees. If this is done, then the excitation light is efficiently irradiated on the examined object, 1 and as a result the fluorescence is also efficiently received by the light detector 3, so the precision of detection is improved.

The operation of the fluorescence detection apparatus of the first embodiment will now be described.

The excitation light emitted from the excitation light source 2, in this example, only ultraviolet light is irradiated in the glass block 4 from a direction perpendicular to the incidence face 5 of the glass block 4. The excitation light (ultraviolet light) incident in the glass block 4 is reflected at the reflection and emission face 6 and deflected 90 degrees to reach the detection face 7. It passes through the detection face 7 and is irradiated on the examined object 1. At this time, part of the excitation light is reflected at the detection face 7 and the surface of the examined object 1, passes through the glass block 4, and returns to the reflection and emission face 6, but the returning light is reflected at the reflection and emission face 6 and heads in the direction of the incidence face 5, so is not emitted outside from the reflection and emission face 6 at the outer side of which the light detector 3 is disposed. That is, the ultraviolet light is not incident on the light detector 3. The fluorescence emitted from the fluorescent substance of the examined object 1 under irradiation by the excitation light passes through the detection face 7 and is incident into the glass block 4. The fluorescence incident into the glass block 4 reaches the reflection and emission face 6 and passes through the reflection and emission face 6 to be emitted outside. At this time, the light reflected at the detection face 7 and the surface of the examined object 1 and returning to the reflection and emission face 6 (ultraviolet light) is not emitted from the reflection and emission face 6 to the outside, so only the fluorescence is emitted from the reflection and emission face 6. The fluorescence emitted from the reflection and emission face 6 is detected by the light detector 3.

when there is no fluorescent substance included in the examined object 1, no fluorescence is emitted from the examined object 1, even if excitation light (ultraviolet light) is irradiated to the examined object 1, so the light detector 3 does not detect any fluorescence.

A judgement apparatus (not shown) discriminates the presence of fluorescence detected by the light detector 3 and the pattern of the same and thereby judges the genuineness of the examined object 1.

As explained above, the fluorescence detection apparatus shown in FIG. 3 is substantially the same in basic function as the fluorescence detection apparatus illustrated in FIG. 1 and FIG. 2, but the fluorescence detection apparatus shown in FIG. 3 uses a single glass block 4 of an angular columnar shape which does not fluoresce under ultraviolet light, so the following effects are exhibited:

(a) It is possible to achieve precision of the glass block just by raising the precision of the machining, including the polishing step, of the glass block 4 and so the design of the optical system becomes easier.

(b) The construction of the optical system becomes simpler, the positioning and affixing of the glass block 4 become easier, and the space required for disposition of the optical system becomes smaller than with optical systems comprised of a plurality of components as in the past, so it is possible to make the fluorescence detection apparatus compact.

(c) The optical system is comprised solely of the glass block 4, so the number of times the excitation light and the fluorescence pass through media with different indexes of refraction becomes fewer and the loss occurring each time different media are passed through becomes smaller as well.

(d) The excitation light can be irradiated perpendicularly to the detected face of the examined object 1, so the problem in the fluorescence detection apparatus of FIG. 1 and FIG. 2 of the effects of the change of the length of the optical path and the change of the optical axis due to the changing distance from the detection window 106 to the examined object 103 caused by transport vibration etc. of the examined object 103 can be minimized.

(e) Further, the fluorescence detection apparatus of the first embodiment has the excitation light source 2 disposed in the lateral direction of the glass block 4, so the height of the fluorescence detection apparatus can be reduced.

(f) Further, the detection face 7 of the glass block 4 performs the function of the detection window 106, that is, the function of suppressing vibration during transport of the examined object 1.

The second embodiment of the fluorescence detection apparatus of the present invention will now be explained with reference to FIGS. 5A and 5B. The fluorescence detection apparatus of the second embodiment is a modification of the first embodiment.

Figure 5A:
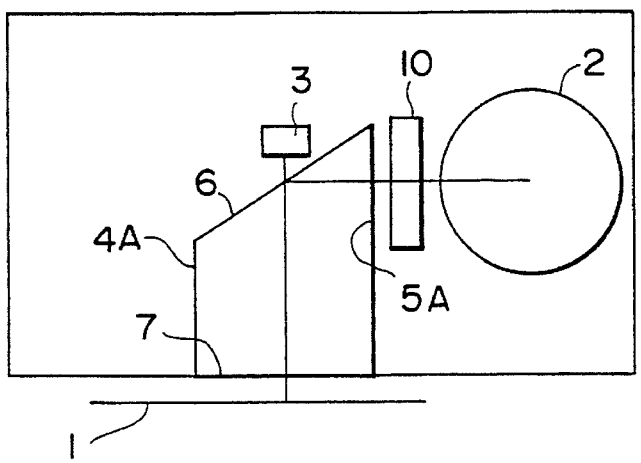

The fluorescence detection apparatus shown in FIG. 5A basically is the same as that shown in FIG. 3. The point of difference from the fluorescence detection apparatus shown in FIG. 3 is the provision of the glass block 4A shown in FIG. 5A, the glass block 4 shown in FIG. 3, and the filter 10 in the fluorescence detection apparatus shown in FIG. 5A. That is, in the fluorescence detection apparatus shown in FIG. 5A, the function of an optical filter blocking the visible light component included in the excitation light from the excitation light source 2 and passing the ultraviolet light region is not given to the incidence face 5A of the glass block 4A. That function is given to the filter 10, which filter 10 is disposed in front of the incidence face 5A. That is, the incidence face 5A of the glass block 4 is merely a glass face.

If the glass block 4A and the filter 10 of FIG. 5A are combined, the optical characteristic, that is, the blocking of visible light, is substantially the same as that of the glass block 4 shown in FIG. 3, so the fluorescence detection apparatus shown in FIG. 3 and the fluorescence detection apparatus shown in FIG. 5A overall exhibit substantially the same operation and effect.

Figure 5B:
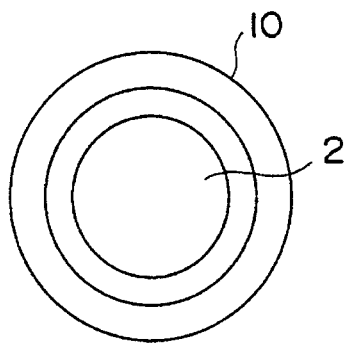

As the filter 10 for passing the ultraviolet light and blocking the visible light, as shown in FIG. 5B, use may be made of one of a shape which covers the entire surface of the excitation light source 2, for example, a cylindrical filter which covers a cylindrical excitation light source 2.

The third embodiment of the fluorescence detection apparatus of the present invention will now be described with reference to FIG. 6.

Figure 6:
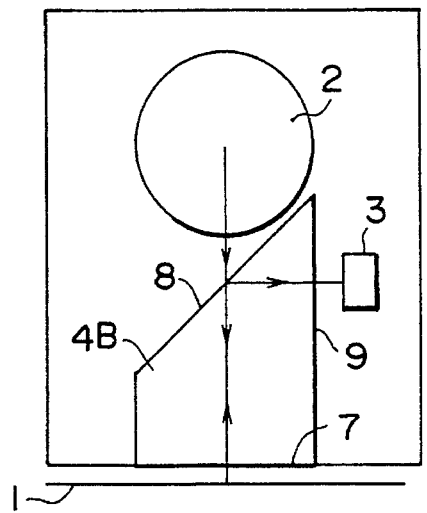
FIG. 6 is a view of the configuration of a third embodiment of the fluorescence detection apparatus of the present invention.

The embodiment shown in FIG. 6 is one where the size of the external dimensions in the direction of transport of the examined object 1 is reduced by disposing the excitation light source 2, which has the largest external dimensions in the fluorescence detection apparatus, above the glass block 4B. That is, this fluorescence detection apparatus becomes higher, but shorter in dimensions in the direction of transport of the examined object 1.

By changing the position of disposition of the excitation light source 2 with respect to the glass block 4B, the position of disposition of the light detector 3 is also changed. That is, the excitation light source 2 and the light detector 3 are disposed at reverse positions.

Along with a change in the positions of the excitation light source 2 and the light detector 3, the glass block B also differs from the glass block 4 shown in FIG. 3 and the glass block 4A shown in FIG. 5A. Of course, the glass block 4B shown in FIG. 6, like the glass blocks 4 and 4A, is one which does not fluoresce under ultraviolet light, is made of synthetic quartz glass, for example, and is shaped like an angular column with one inclined face.

As shown in FIG. 4, the glass block 4B is shaped the same as the glass blocks 4 and 4A, but differs in the faces.

The face defined by the ABDC face of the glass block 4B is made the incidence and reflection face 8. This incidence and reflectance face 8 is provided by evaporation etc. with a film having a filtering function blocking the visible light component of the excitation light from the excitation light source 2 incident on the same and passing only ultraviolet light and also, reflecting the fluorescence emitted from the fluorescent substance of the examined object 1.

The detection face 7 defined by the EFHG face of the glass block 4B is substantially the same as the detection face 7 in the glass block 4. The detection face 7 is disposed near to and parallel with the examined object 1 and further passes the excitation light (ultraviolet light) incident from the incidence and reflection face 8 to irradiate the same on the examined object 1. Further, it allows passage of the fluorescence emitted from the fluorescent substance of the examined object 1 under the irradiation.

The emission face 9 defined by the ABFE face of the glass block 4B allows passage of the fluorescence passing through the detection face 7 and reflected at the incidence and reflection face 8.

Note that in the third embodiment as well, the glass block 4B is made in an angular columnar shape and the detection face 7 is disposed close to and parallel with the detected face of the examined object 1, so the excitation light emitted from the detection face 7 is irradiated perpendicularly with respect to the detected face of the examined object 1.

The operation of the fluorescence detection apparatus of the third embodiment will now be explained.

The excitation light including the visible light from the excitation light source 2 is incident on the incidence and reflection face 8 of the glass block 4B. Only the ultraviolet light passes through the glass block 4B and reaches the detection face 7. The ultraviolet light passing through the detection face 7 acts on the fluorescent substance of the examined object 1 to cause fluorescence. The fluorescence passes through the detection face 7, passes through the glass block 4B, is reflected at the inside face of the incidence and reflection face 8, heads toward the emission face 9, passes through the emission face 9, and is made incident on the light detector 3.

The treatment of the fluorescence incident on the light detector 3 in the judgement apparatus is the same as the first and second embodiments.

Since the excitation light (ultraviolet light) from the excitation light source 2 is made incident on the incidence and reflection face 8 of the glass block 4B at an angle of 45 degrees, and the angle formed by the optical axis of the excitation light incident on the examined object 1 becomes 90 degrees, the fluorescence from the examined object 1 becomes superimposed on the same line as the optical axis of the excitation light to the detection face 1 except reversed in direction 180 degrees. As a result, the excitation light is efficiently irradiated on the examined object 1 and as a result the fluorescence is also efficiently received by the light detector 3, so the precision of detection is improved.

The fluorescence detection apparatus of the third embodiment has a smaller size in the direction of transport of the examined object 1 and is higher in the height direction but otherwise exhibits a similar effect to those described in the first and second embodiments.

Next, an explanation will be given of the fourth embodiment of the fluorescence detection apparatus of the present invention.

In the above-mentioned embodiments, the fluorescence emitted from the fluorescent ink or fluorescent whitener on the surface of the examined object 1 (reflected fluorescence) was detected at the same side as the irradiation of the excitation light, so these could not sufficiently detect the fluorescence of fluorescent threads woven into the examined object 1. The fourth embodiment solves this problem. That is, the fourth embodiment provides a fluorescence detection apparatus which can detect both the reflected fluorescence and the transmitted fluorescence emitted from the fluorescent substance of the examined object 1 to enable accurate detection, uses few components, and can be made compact in size.

The fourth embodiment of the fluorescence detection apparatus of the present invention will next be explained with reference to FIG. 7. The fluorescence detection apparatus shown in FIG. 7, like with the first embodiment, reduces the height of the fluorescence detection apparatus perpendicularly intersecting the direction of transport of the examined object 1 by providing the large outer dimension excitation light source 2 at the side of the glass block 4.

The excitation light source 2, the light detector 3, and the glass block 4 are respectively substantially the same as the excitation light source 2, the light detector 3, and the glass block 4 shown in FIG. 3. The light detector 3 used is for example an opto-electric (O/E) converter able to receive light of the wavelength band of the fluorescence which is disposed at the outer side of the reflection and emission face 6 and further is oriented in a direction coaxial with the optical axis of the excitation light from the first excitation light source 2 of the front side (top of the figure) and the optical axis of the excitation light from the second excitation light source 12 at the reverse side (bottom of the figure), explained later.

Figure 7:
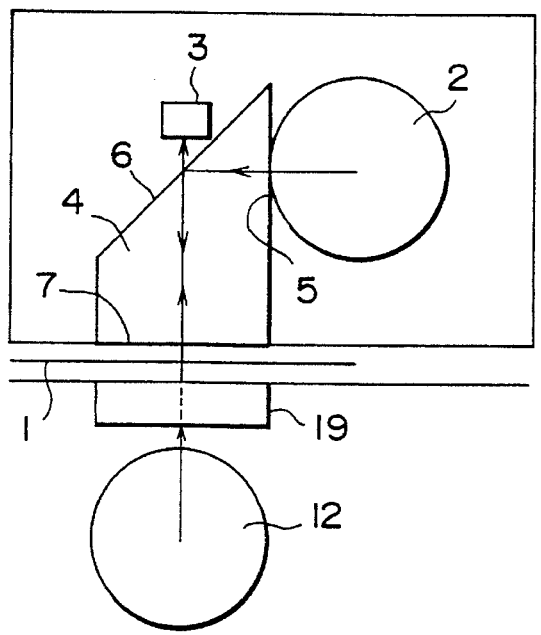
FIG. 7 is a view of the configuration of a fourth embodiment of the fluorescence detection apparatus of the present invention.

The fluorescence detection apparatus shown in FIG. 7 is further provided with an optical filter 19 and a second excitation light source 12.

The second excitation light source 12 is substantially the same as the excitation light source 2 and emits light including ultraviolet light. For example, use may be made of a black light, a UV lamp, etc.

The optical filter 19 is disposed between the rear side of the examined object 1 and the rear side second excitation light source 12. This optical filter 19 has a filtering function blocking the visible light component of the excitation light emitted from the second excitation light source 12 and passing only the ultraviolet component. That is, the optical filter 19 is substantially the same as the filter 10 in the second embodiment.

The operation of the fluorescence detection apparatus shown in FIG. 17 will be described next.

The excitation light emitted from the excitation light source 2 strikes the incidence face 5 of the glass block 4, where the visible light component is blocked and only the ultraviolet region is passed to be incident in the glass block 4. The excitation light (ultraviolet component) incident in the glass block 4 is reflected at the reflection and emission face 6 and reaches the detection face 7, then passes through the detection face 7 and irradiates the examined object 1. At this time, part of the excitation light (ultraviolet component) is reflected at the detection face 7 and the surface of the examined object 1 and returns to the reflection and emission face 6, but the returning light is reflected at the reflection and emission face 6, so is not emitted from the reflection and emission face 6 to the outside light detector 3. The fluorescence (reflected fluorescence) emitted from the fluorescent substance of the examined object 1 under irradiation of the excitation light (ultraviolet component) passes through the detection face 7 and is made incident inside the glass block 4. The reflected fluorescence incident inside the glass block 4 reaches the reflection and emission face 6, passes through it, is emitted to the outside, and is incident on the light detector 3. At this time, the light reflected at the detection face 7 and the surface of the examined object 1 and returning to the reflection and emission face 6 is not emitted to the outside from the reflection and emission face 6, so only the reflected fluorescence is emitted from the reflection and emission face 6. The reflected fluorescence emitted from the reflection and emission face 6 is detected by the light detector 3. Further, the excitation light emitted from the second excitation light source 12 strikes the optical filter 19, where the visible light component is blocked and only the ultraviolet component passes, and subsequently passes through the examined object 1. At this time, fluorescence (transmitted fluorescence) is emitted from the fluorescent substance of the examined object 1 and is made incident in the glass block 4. The transmitted fluorescence incident in the glass block 4 reaches the reflection and emission face 6 of the glass block 4 and passes through the same to be emitted outside. The emitted transmitted fluorescence is detected by the light detector 3.

In this way, the light detector 3 receives both the fluorescence generated by the irradiation of the ultraviolet light from the excitation light source 2 on the examined object 1 and the fluorescence generated by the passage of the ultraviolet light from the second excitation light source 2 through the examined object 1.

Accordingly, in addition to the fluorescence (reflected fluorescence) emitted from the fluorescent ink or fluorescent whitener on the surface of the examined object 1 detected using the excitation light source 2, glass block 4, and light detector 3, it is possible to detect the fluorescence in the case of fluorescent thread woven in the examined object 1 using the second excitation light source 12, the optical filter 19, the glass block 4, and the light detector 3.

The fluorescence detection apparatus of the fourth embodiment is able to detect both the reflected fluorescence from the surface of the examined object and the transmitted fluorescence passing through the examined object 1 within the same range, so the precision of detection is improved. Further, the fluorescence detection apparatus of the fourth embodiment shares the glass block and the light detector 3, so the number of components becomes smaller and two functions can be realized by a simple construction. That is, the fluorescence detection apparatus of the fourth embodiment enables accurate detection by detecting both the reflected fluorescence and the transmitted fluorescence emitted from the fluorescent substance of the examined object 1 and further realizes a smaller number of components and a smaller size.

A modification of the fourth embodiment of the fluorescence detection apparatus of the present invention is described next as a fifth embodiment. The fluorescence detection apparatus of this fifth embodiment is substantially the same as the second embodiment, which was a modification of the fluorescence detection apparatus of the first embodiment.

Figure 8:
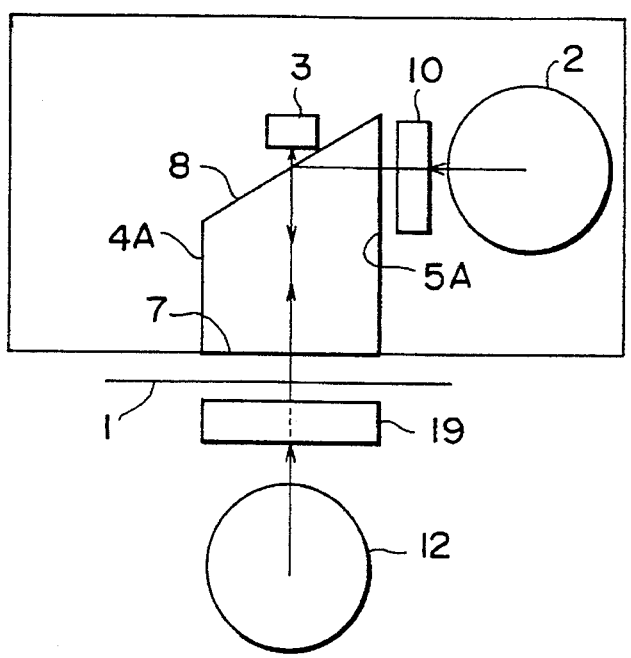
FIG. 8 is a view of the configuration of a fifth embodiment of the fluorescence detection apparatus of the present invention.

FIG. 8 is a view of the configuration of the fifth embodiment of the fluorescence detection apparatus of the present invention.

In the fluorescence detection apparatus shown in FIG. 7, the incidence face 5 of the glass block 4 was given a filtering function for blocking the visible light, but in the fluorescence detection apparatus shown in FIG. 8, the incidence face 5A of the glass block 4A is not given a visible light blocking function. Rather, a filter 10 having the function of blocking visible light is disposed separate from the glass block 4A (incidence face 5A) between the incidence face 5A and the excitation light source 2.

The second excitation light source 12 and optical filter 19 are the same as in the fourth embodiment.

The sixth embodiment of the fluorescence detection apparatus of the present invention will now be described with reference to FIG. 9.

Figure 9:
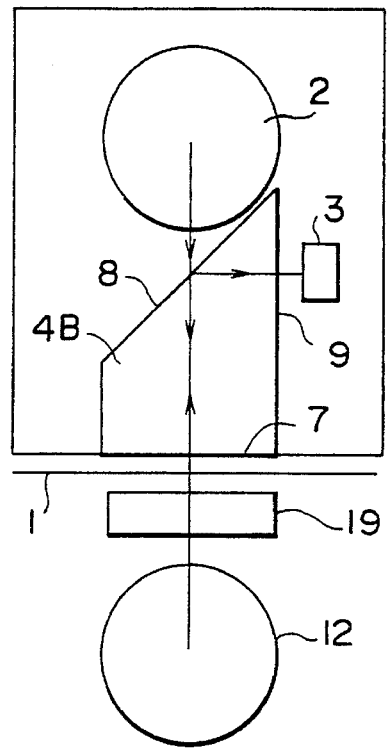
FIG. 9 is a view of the configuration of a sixth embodiment of the fluorescence detection apparatus of the present invention.

FIG. 9 shows the configuration of the fluorescence detection apparatus of the sixth embodiment.

This fluorescence detection apparatus holds down the outside dimension in the direction of transport of the examined object 1 by disposing the large outer dimension excitation light source 2 above the glass block 4B. In this regard, the embodiment is substantially the same as the fluorescence detection apparatus of the third embodiment described with reference to FIG. 6.

The glass block 4B shown in FIG. 9, like with the glass block 4B shown in FIG. 6, has an incidence and reflection face 8, an emission face 9, and a detection face 7. The optical transmission characteristics of these faces differ from the optical transmission characteristics of the glass blocks 4 and 4A shown in FIG. 7 and FIG. 8. Other basic matters are similar to those of the fourth and fifth embodiments.

The operation of the fluorescence detection apparatus shown in FIG. 9 will now be explained.

The excitation light emitted from the excitation light source 2 strikes the incidence and reflection face 8 of the glass block 4B where the visible light component is blocked and only the ultraviolet region passes to be incident on the glass block 4B. The excitation light (ultraviolet component) incident in the glass block 4B proceeds through the glass block 4B to reach the detection face 8 and passes through the detection face 7 to irradiate the examined object 1. At this time, part of the excitation light (ultraviolet component) is reflected at the detection face 7 and the surface of the examined object 1 and returns to the incidence and reflection face 8, but this passes through the incidence and reflection face 8 which has a filtering function passing the ultraviolet component of the excitation light and is emitted to the excitation light source 2 side, so is not reflected at the incidence and reflection face 8 and is not emitted from the emission face 9 toward the light detector 3. The reflected fluorescence emitted from the fluorescent substance of the examined object I under irradiation of the excitation light (ultraviolet light) passes through the detection face 7 and is made incident inside the glass block 4B. The reflected fluorescence incident inside the glass block 4B reaches the incidence and reflection face 8 and is reflected there and emitted to the outside from the emission face 9. The reflected fluorescence emitted is detected by the light detector 3.

The excitation light emitted from the second excitation light source 12 strikes the optical filter 19, where the visible light component is blocked and only the ultraviolet light component passes, and subsequently passes through the examined object 1. At this time, fluorescence (transmitted fluorescence) is emitted from the fluorescent substance of the examined object 1 and is made incident in the glass block 4B. The transmitted fluorescence incident in the glass block 4B reaches the incidence and reflection face 8 of the glass block 4B, is reflected there, and is emitted outside of the glass block 4B from the emission face 9. The emitted transmitted fluorescence is detected by the light detector 3.

The seventh embodiment of the fluorescence detection apparatus of the present invention will next be explained.

Figure 10A:
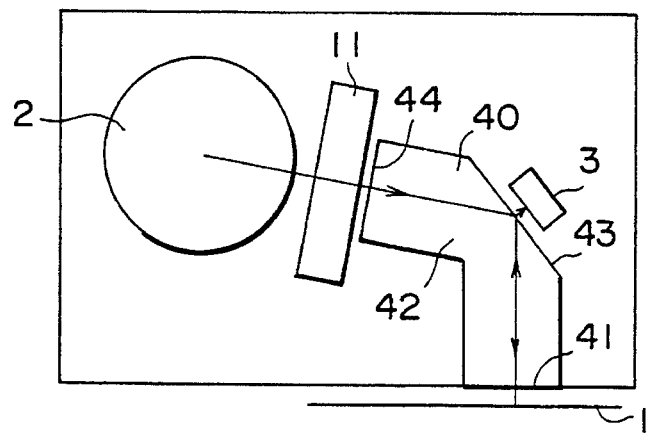
FIGS. 10A and 10B are views of the configuration of a seventh embodiment of the fluorescence detection apparatus of the present invention.
Figure 10B:
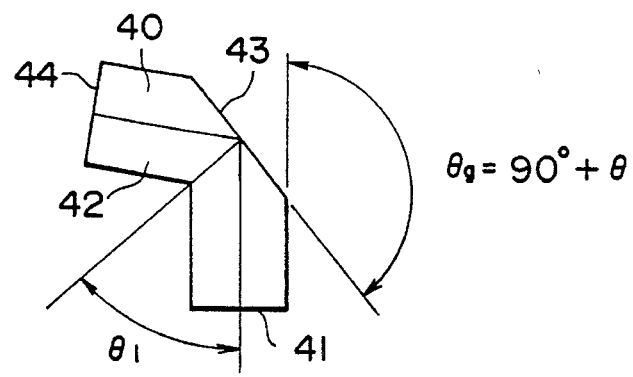
Figure 11:
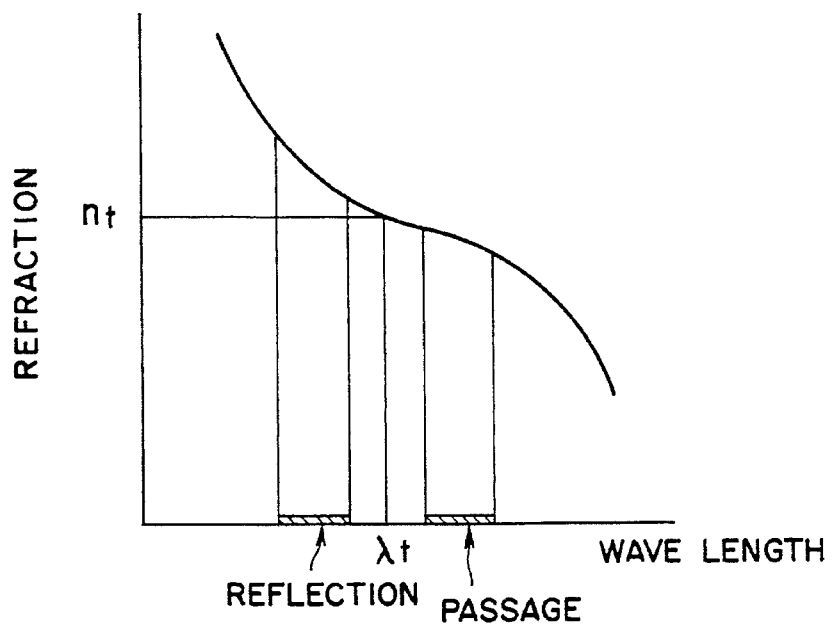
FIG. 11 is a graph of the index of refraction of the glass block in the fluorescence detection apparatus of the seventh embodiment shown in FIGS. 10A and 10B.

The configuration of the seventh embodiment of the fluorescence detection apparatus of the present invention is shown in FIGS. 10A and 10B.

The fluorescence detection apparatus has an excitation light source 2, an optical filter 11, a glass block 40, and a light detector 3.

In this fluorescence detection apparatus, the height with respect to the transport direction of the examined object 1 is held down by disposing the large outer dimension excitation light source 2 at the side of the glass block 40.

The examined object 1 is for example a paper etc. containing a fluorescent substance. As the excitation light source 2, use is made for example of a black light, UV lamp, etc. The light detector 3 is disposed at the outside of the inclined face 43 of the glass block 40. As the light detector 3, use is made for example of an opto-electric (O/E) converter able to receive the wavelength band of fluorescence.

The glass block 40 is disposed between the optical filter 11 and the examined object 1 and light detector 3 and optically couples the same. The glass block 40 is made of a synthetic quartz glass which does not fluoresce under ultraviolet light.

The glass block 40 is shaped as an angular column having an L-shaped side section, at one end of which is formed the incidence face 44 and at the opposing end along the optical axis is formed the detection face 41. The inclined face 43 is formed at the outer side face of the bent portion 42.

The angle $\theta_g$ of the inclined face 43 is designed to be an angle at which the light of the wavelength of the excitation light (ultraviolet light) is reflected and light of the wavelength of the fluorescence emitted from the fluorescent substance of the examined object passes. Specifically, the angle $\theta_g$ of the inclined face 43 is determined by selecting it to be equal to the critical angle $\theta_c$ calculated from the following equations based on the index of refraction $n_t$ of the glass block 40 and the index of refraction $n_a$ of the substance between the inclined face 43 of the glass block 40 and the light detector 3, in this example, air.

$$\theta_1 = \theta_c = \sin^{-1}(n_a/n_t) \quad (1)$$

$$\theta_g = 90° + \theta_1 \quad (2)$$
$$= 90° + \sin^{-1}(n_a/n_t)$$

By selecting the angle $\theta_g$ of the inclined face 43 of the glass block 40 to be 90°+$\theta_1$ as mentioned above, the light of the ultraviolet light wavelength (<$\lambda_t$) passing from the excitation light source 2 through the optical filter 11 to be incident in the glass block 40 is completely reflected at the inclined face 43 of the glass block 40 and irradiated on the examined object 1. The light of the wavelength of the visible light region (wavelength of fluorescence >$\lambda_t$) emitted from the fluorescent substance of the examined object 1 under the irradiation passes through the inclined face 43 of the glass block 40 and is made incident on the light detector 3.

The detection face 41 of the glass block 40 is made to face the examined object nearby in parallel with the same and is made so that the excitation light reflected at the inclined face 43 passes through it and the fluorescence emitted from the fluorescent substance of the examined object 1 is incident on it.

The optical filter 11 blocks the visible light component of the excitation light incident there from the excitation light source 2 and passes only the ultraviolet light region. When the excitation light emitted from the excitation light source 1 does not include a visible light component and contains only the ultraviolet light component, there is no need to provide the optical filter 11.

Note that it is also possible not to provide the optical filter 11 and to provide the incidence face 44 of the glass block 40 by evaporation etc. with a film having a filtering function blocking visible light and passing ultraviolet light the same way as the optical filter 11 (film having a filtering function blocking the visible light component of excitation light and passing only the ultraviolet light component).

Further, when the excitation light emitted from the excitation light source 2 does not include a visible light component and includes only an ultraviolet light component, there is no need for giving a filtering function to the incidence face 44 of the glass block 40. Of course, the optical filter 11 also is unnecessary.

The operation of the fluorescence detection apparatus shown in FIG. 10A will be explained next.

The fluorescence detection apparatus of this embodiment reflects the wavelength of the excitation light at the outside face of the bent portion 42 of the glass block 40, but forms an inclined face 43 of an angle passing the wavelength of the fluorescence emitted from the fluorescent substance.

The excitation light emitted from the excitation light source 2 passes through the optical filter 11 and is incident from the incidence face 44 of the glass block to the inside of the glass block 40. At this time, the optical filter 11 passes the wavelength of the excitation light, but blocks the unnecessary wavelength, in particular the visible light component. The excitation light incident in the glass block 40 is reflected at the inclined face 43 of the glass block 40, reaches the detection face 41 of the glass block 40, passes through the detection face 41, and irradiates the examined object 1 at an angle of 90 degrees. At this time, part of the excitation light is reflected at the surface of the examined object 1 and returns to the inclined face 43, but the light is reflected at the inclined face 43, and is not emitted to the outside from the inclined face 43. The fluorescence emitted from the fluorescent substance of the examined object 1 under irradiation of the excitation light passes through the detection face 41 and is made incident inside the glass block 40. The fluorescence incident inside the glass block 40 reaches the inclined face 43, passes through the inclined face 43, and is emitted to the outside. At this time, in the same way as above, the light reflected at the surface of the examined object 1 and returning to the inclined face 43 is not emitted to the outside from the inclined face 43 as mentioned earlier, so only the fluorescence is emitted from the inclined face 43. The emitted fluorescence is detected by the light detector 3.

When the examined object 1 does not include a fluorescent substance, no fluorescence is emitted from the examined object 1 even if the excitation light is irradiated, so the light detector 3 does not detect any fluorescence.

In the fluorescence detection apparatus of the eighth embodiment, use is made of the changes in the index of refraction due to the difference in the wavelength of the light so as to pass and reflect by the glass block 40 only the wavelength necessary, so there are the following effects:

(a) No optical filter is required for the wavelength selection, so the optical filter becomes smaller than in the fluorescence detection apparatus of the related art (Japanese Patent Application No. 5-123526), the construction of the optical system becomes simpler, and the cost becomes lower.

(b) The number of optical filters is reduced and it is sufficient to use just a single glass block 40, so the optical design becomes easy as well.

The eighth embodiment of the fluorescence detection apparatus of the present invention will now be explained with reference to FIG. 12.

Figure 12:
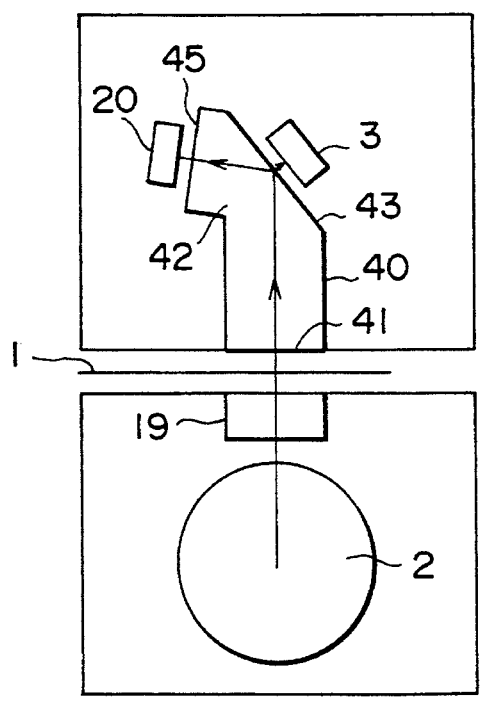
FIG. 12 is a view of the configuration of an eighth embodiment of the fluorescence detection apparatus of the present invention.

The fluorescence detection apparatus of the seventh embodiment shown in FIGS. 10A and 10B was a reflection type fluorescence detection apparatus which reflected the excitation light from the excitation light source 2 and the fluorescence emitted from the examined object 1, but the fluorescence detection apparatus shown in FIG. 12 is a transmission type fluorescence detection apparatus in which the excitation light from the excitation light source 2 and the fluorescence emitted from the examined object 1 passes through the examined object 1.

The transmission type fluorescence detection apparatus shown in FIG. 12 has an excitation light source 2, an optical filter 19, a glass block 40, a light detector 3, and an excitation light detector 20.

The excitation light detector 20 detects the excitation light emitted from the excitation light source 2, passing through the optical filter 19 and examined object 1, and reflected at the inclined face 43 of the glass block 40. The optical filter 19 blocks the visible light component of the light excited by the excitation light source 2 and passes only the ultraviolet light. When the excitation light emitted from the excitation light source 2 does not include a visible light component, the optical filter 11 does not have to be provided.

In this fluorescence detection apparatus, the dimension in the direction of transport of the examined object 1 is minimized by disposing the excitation light source 2 under the L-shaped glass block The operation of the fluorescence detection apparatus shown in FIG. 12 will now be described.

The excitation light emitted from the excitation light source 2 is incident on the optical filter 19 which allows only the ultraviolet light to selectively pass. This ultraviolet light passes through the examined object 1. The fluorescence emitted from the fluorescent substance of the examined object 1 due to the passage of the excitation light (ultraviolet light) is incident inside the glass block 40 from the detection face 41 of the glass block 40. The fluorescence incident inside the glass block 40 passes through the inclined face 43 of the glass block 40 and is detected by the light detector 3.

The excitation light (ultraviolet light) incident inside the glass block 40 is reflected at the inclined face 43 of the glass block 40 and reaches the emission face 45 of the glass block 40. It passes through the emission face 45 and is detected by the excitation light detector 20.

When there is no fluorescent substance included in the examined object 1, no fluorescence is emitted from the examined object 1 even if excitation light (ultraviolet light) is irradiated to the examined object 1, so the light detector 3 does not detect any fluorescence.

In this fluorescence detection apparatus, it is possible in the excitation light detector 20 to also detect the excitation light (ultraviolet light) passing through the examined object 1, so it is also possible to detect the thickness of the examined object 1, the material dirtiness, etc. from the difference between the intensity of the excitation light detected and the intensity of the excitation light output from the excitation light source 2.

The fluorescence detection apparatus of the present invention is not limited to the above-described examples and may take the form of various modifications of the above-mentioned embodiments. Further, the above-mentioned embodiments may be suitably combined as well.

We claim:

1. A fluorescence detection apparatus for differentiating an object containing a fluorescent substance by detecting fluorescence emitted by said fluorescent substance, said apparatus comprising:

an excitation light source which emits ultraviolet light that excites a fluorescent substance, said ultraviolet light being filtered or non-filtered;

a light detector for detecting fluorescence; and an optical guiding system for guiding said ultraviolet light to an object containing a fluorescent substance thereon, and for guiding fluorescence emitted by said fluorescent substance excited by said ultraviolet light to said light detector for differentiating said object, said optical guiding system consisting essentially of a single glass block which does not fluoresce under ultraviolet light, said single glass block being of an angular columnar shape having an inclined face, said single glass block comprising:

an incidence face located on a side of said glass block, through which said ultraviolet light enters;

a reflection and emission face constituted by said inclined face, from which said incident ultraviolet light reflects toward said object, and through which florescence emitted from said object passes toward said light detector, said reflection and emission face being treated to reflect ultraviolet light and pass fluorescence; and a detection face at the bottom of said glass block facing said object, through which said ultraviolet light exits and hits said object, and through which fluorescence emitted from said object enters, said detection face being treated to pass ultraviolet light and pass fluorescence.

2. A fluorescence detection apparatus as set forth in claim 1, wherein the incidence face of the glass block is treated to pass only ultraviolet light.

3. A fluorescence detection apparatus as set forth in claim 1, wherein an optical filter passing only ultraviolet light is provided between the incidence face of the glass block and the excitation light source.

4. A fluorescence detection apparatus which irradiates ultraviolet light to an examined object including a fluorescent substance to cause it to emit fluorescence and which detects that fluorescence, said apparatus comprising:

a single glass block of an angular columnar shape which does not fluoresce under ultraviolet light and has one inclined face and which has an incidence and reflection face constituted by the inclined face, a flat detection face which substantially faces the incidence and reflection face and perpendicularly intersects with a longitudinal direction of the angular columnar shape, and an emission face which continues from the incidence and reflection face to the detection face;

an excitation light source which emits light including ultraviolet light and which is provided near the incidence and reflection face of the glass block so that the light from the excitation light source is made incident on the glass block from the incidence and reflection face;

a light detector which is provided near the emission face of the glass block so as to receive light from the emission face;

the detection face of the glass block being made to face a flat examined object including a fluorescent substance;

the incidence and reflection face of the glass block being treated to pass ultraviolet light and reflect fluorescence;

the detection face of the glass block being treated to pass ultraviolet light and pass fluorescence; and the emission face of the glass block being treated to reflect ultraviolet light and pass fluorescence.

5. A fluorescence detection apparatus for differentiating an object containing a fluorescent substance by detecting fluorescence emitted by said fluorescent substance, said apparatus comprising:

an excitation light source which emits ultraviolet light that excites a fluorescent substance, said ultraviolet light being filtered or non-filtered;

a light detector for detecting fluorescence;

an optical guiding system for guiding said ultraviolet light to an object containing a fluorescent substance thereon, and for guiding fluorescence emitted by said fluorescent substance excited by said ultraviolet light to said light detector for differentiating said object, said optical guiding system consisting essentially of a single glass block which does not fluoresce under ultraviolet light, said single glass block being of an angular columnar shape having an inclined face, said single glass block comprising:

an incidence face located on a side of said glass block, through which said ultraviolet light enters;

a reflection and emission face constituted by said inclined face, on which said incident ultraviolet light reflects toward said object, and through which fluorescence emitted from said object passes toward said light detector, said reflection and emission face being treated to reflect ultraviolet light and pass fluorescence; and a detection face at the bottom of said glass block facing said object, through which said ultraviolet light exits and hits said object, and through which fluorescence emitted from said object enters, said detection face being treated to pass ultraviolet light and pass fluorescence; and a second excitation light source which emits ultraviolet light that excites a fluorescent substance, said ultraviolet light being filtered or non-filtered, said second excitation light source disposed on the other side of said object opposite to said detection face of said glass block, said ultraviolet light causing said fluorescent substance of said object to be excited and emit fluorescence which enters said glass block through said detection face thereof and exits said glass block through said reflection and emission face thereof toward said light detector together with said fluorescence caused by said first excitation light source.

6. A fluorescence detection apparatus as set forth in claim 5, wherein provision is made, between the second excitation light source and the examined object, of a second optical filter for blocking the visible light component included in the light emitted from the second excitation light source and allowing only the ultraviolet light to irradiate the examined object.

7. A fluorescence detection apparatus as set forth in claim 6, wherein the incidence face of the glass block is treated to pass only ultraviolet light.

8. A fluorescence detection apparatus as set forth in claim 6, wherein an optical filter passing only ultraviolet light is provided between the incidence face of the glass block and the excitation light source.

9. A fluorescence detection apparatus which irradiates ultraviolet light to an examined object including a fluorescent substance to cause it to emit fluorescence and detects that fluorescence, said apparatus comprising:

a single glass block of an angular columnar shape which does not fluoresce under ultraviolet light and has one inclined face and which has an incidence and reflection face constituted by the inclined face, a flat detection face which substantially faces the incidence and reflection face and perpendicularly intersects with a longitudinal direction of the angular columnar shape, and an emission face which continues from the incidence and reflection face to the detection face;

an excitation light source which emits light including ultraviolet light and which is provided near the incidence and reflection face of the glass block so that the light from the excitation light source is made incident on the glass block from the incidence and reflection face;

a light detector which is provided near the emission face of the glass block so as to receive fluorescence from the emission face; and a second excitation light source which is provided at a position facing the detection face of the glass block sandwiching the examined object and which emits light including ultraviolet light;

the detection face of the glass block being made to face a flat examined object including a fluorescent substance;

the incidence and reflection face of the glass block being treated to pass ultraviolet light and reflect fluorescence;

the detection face of the glass block being treated to pass ultraviolet light and pass fluorescence; and the emission face of the glass block being treated to reflect the ultraviolet light and pass fluorescence.

10. A fluorescence detection apparatus as set forth in claim 9, wherein provision is made, between the second excitation light source and the examined object, of a second optical filter for blocking the visible light component included in the light emitted from the second excitation light source and allowing only the ultraviolet light to irradiate the examined object.

11. A fluorescence detection apparatus which irradiates ultraviolet light to an examined object including a fluorescent substance to cause it to emit fluorescence and detects that fluorescence, which apparatus is provided with:

a single bent glass block which does not fluoresce under ultraviolet light, is provided with an inclined face at a center bent portion, has an incidence face formed at one of the end faces of the glass block bent at the bent portion so as to receive the ultraviolet light, has a detection face formed at the other end face of the glass block bent at the bent portion so as to pass ultraviolet light and fluorescence, and has an angle $\theta_g$ of the inclined face defined so as to reflect the ultraviolet light and pass the fluorescence;

an excitation light source which emits light including ultraviolet light and which is provided near the incidence face of the glass block so that the light from the excitation light source is made incident on the glass block from the incidence face; and a light detector which is provided near the inclined face of the glass block so as to receive fluorescence from the inclined face;

the detection face of the glass block being made to face a flat examined object including a fluorescent substance.

12. A fluorescence detection apparatus as set forth in claim 11, wherein the angle $\theta_g$ of the inclined face is defined by the following equation:

$$\theta_g = 90° + \sin^{-1}(n_a/n_t)$$

where, $n_a$ is the index of refraction of the medium between the inclined face and the light detector and $n_t$ is the index of refraction of the glass block.

13. A fluorescence detection apparatus as set forth in claim 12, wherein the incidence face of the glass block is treated to block the visible light component included in the light emitted from the excitation light source and to pass only the ultraviolet light component.

14. A fluorescence detection apparatus as set forth in claim 12, wherein provision is made, between the excitation light source and the incidence face of the glass block, of an optical filter for blocking the visible light component included in the light emitted from the excitation light source and allowing only the ultraviolet light component to pass.

15. A fluorescence detection apparatus which irradiates ultraviolet light to an examined object including a fluorescent substance to cause it to emit fluorescence and detects that fluorescence, said apparatus comprising:

a bent single glass block which does not fluoresce under ultraviolet light, is provided with an inclined face at a center bent portion, has an emission face formed at one of the end faces of the glass block bent at the bent portion so as to pass the ultraviolet light, has a detection face formed at the other end face of the glass block bent at the bent portion so as to pass ultraviolet light and fluorescence, and has an angle $\theta_g$ of the inclined face defined so as to reflect the ultraviolet light and pass the fluorescence, an excitation light source which emits light including ultraviolet light and which is provided at a position facing the detection face of the glass block sandwiching the examined object including the fluorescent substance so as to irradiate ultraviolet light to the examined object, a light detector which is provided near the inclined face of the glass block so as to receive fluorescence from the inclined face, and an excitation light detector provided near the emission face of the glass block so as to receive the ultraviolet light from the emission face, the detection face of the glass block being made to face the examined object.

16. A fluorescence detection apparatus as set forth in claim 15, wherein the angle $\theta_g$ of the inclined face is defined by the following equation:

$$\theta_g = 90° + \sin^{-1}(n_a/n_t)$$

where, $n_a$ is the index of refraction of the medium between the inclined face and the light detector and $n_t$ is the index of refraction of the glass block.

17. A fluorescence detection apparatus as set forth in claim 16, wherein provision is made, between the excitation light source and the examined object, of an optical filter for blocking the visible light component included in the light emitted from the excitation light source and allowing only the ultraviolet light component to pass.

* * * * *

UNITED STATES PATENT AND TRADEMARK OFFICE
CERTIFICATE OF CORRECTION

PATENT NO. : 5,512,758
DATED : April 30, 1996
INVENTOR(S) : Takao Kobayashi, et al It is certified that error appears in the above-indentified patent and that said Letters Patent is hereby corrected as shown below:

On the title page item [73], should read -- The Furukawa Electric Co., Ltd., Tokyo Japan

Signed and Sealed this

Twenty-fourth Day of September, 1996

Attest:

BRUCE LEHMAN

Attesting Officer      Commissioner of Patents and Trademarks